(12) United States Patent
Nakamura Labastida et al.

(10) Patent No.: US 9,621,071 B2
(45) Date of Patent: Apr. 11, 2017

(54) HIGH POWERED CURRENT GENERATOR FOR ELECTROMAGNETIC INSPECTION OF HYDROCARBON PIPELINES

(71) Applicant: INSTITUTO MEXICANO DEL PETROLEO, Mexico City (MX)

(72) Inventors: Edgar Kiyoshi Nakamura Labastida, Mexico City (MX); Aleksandr Mousatov, Mexico City (MX); Alberto Flores Roa, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 14/602,785

(22) Filed: Jan. 22, 2015

(65) Prior Publication Data

US 2015/0214855 A1    Jul. 30, 2015

(30) Foreign Application Priority Data

Jan. 24, 2014   (MX) .................... MX/a/2014/000944

(51) Int. Cl.
*H02M 7/44*      (2006.01)
*H02M 5/458*     (2006.01)
(Continued)

(52) U.S. Cl.
CPC .............. *H02M 7/44* (2013.01); *H02M 5/458* (2013.01); *G01N 17/02* (2013.01); *H02M 2001/007* (2013.01)

(58) Field of Classification Search
CPC ............... H02M 7/44; H02M 7/53803; H02M 2001/007; H02M 5/458; H02J 3/1835;
(Continued)

(56) References Cited

U.S. PATENT DOCUMENTS 6,051,977 A     4/2000  Masuda et al.
6,091,232 A *   7/2000  Criscione .............. H02M 3/158
                                                 323/222
(Continued)

*Primary Examiner* — Jessica Han
*Assistant Examiner* — Demetries A Gibson
(74) *Attorney, Agent, or Firm* — Dickinson Wright PLLC

(57) ABSTRACT

A high powered current generator for electromagnetic inspection of hydrocarbon pipelines from an AC stabilized with rectangular waveform and whose measurements and interpretation are used for evaluating the condition of the lining of the pipelines of five main modules: self-programmable regulated voltage power source module; power source reference decoupling module; H Bridge inverter module; feedback module, and control and processing module. The generator was specifically designed as part of the instrumentation of (TIEMS); which supplies an electric current in the pipeline to produce electromagnetic radiation along the hydrocarbon pipeline. This energy is detected by antennas for obtaining the location of the pipeline and the electric current flowing therein. The generator produces an alternating current at a frequency that can be set within the range of 0.1 Hz to 1 KHz. However, to simplify the job of the operating personnel, default values of 0.1, 0.2, 0.05, 1, 2, 4, 8, 98, 512 and 625 Hertz were established. The current value can also be programmed within the range of 0.1 A to 4.5 A. In order to facilitate the work of the operators, a set of fixed current values 0.100, 0.250, 0.500, 1.0, 1.5, 2.0, 2.5, 3, 3.5, 4.0 and 4.5 Amperes was established.

5 Claims, 5 Drawing Sheets

(51) Int. Cl.
*G01N 17/02* (2006.01)
*H02M 1/00* (2006.01)

(58) Field of Classification Search
CPC ... H02J 3/48; H02J 2003/388; Y10T 307/544; Y10T 307/406; Y02E 40/30
USPC ............ 363/283, 284; 324/700, 71.1; 374/7; 73/627
See application file for complete search history.

(56) References Cited

U.S. PATENT DOCUMENTS

| | | | |
|---|---|---|---|
| 6,836,231 B2* | 12/2004 | Pearson | G01R 29/085 324/624 |
| 7,541,817 B2* | 6/2009 | Nielsen | G01N 17/02 166/250.05 |
| 8,000,936 B2* | 8/2011 | Davis | G01N 17/02 137/559 |
| 2002/0196160 A1* | 12/2002 | Hilleary | C23F 13/22 3/22 |
| 2003/0147186 A1* | 8/2003 | Schultz | H02P 9/305 361/15 |
| 2005/0038489 A1* | 2/2005 | Grill | A61N 1/05 607/116 |
| 2007/0035315 A1* | 2/2007 | Hilleary | G01N 17/02 324/700 |
| 2008/0163692 A1* | 7/2008 | Huang | G01F 1/663 73/627 |
| 2008/0204274 A1* | 8/2008 | Peters | G08C 19/02 340/870.07 |
| 2012/0038376 A1* | 2/2012 | Shukla | G01N 17/02 324/700 |

* cited by examiner

HIGH POWERED CURRENT GENERATOR FOR ELECTROMAGNETIC INSPECTION OF HYDROCARBON PIPELINES

CROSS-REFERENCE TO RELATED APPLICATION

This application claims the benefit and priority under 35 U.S.C. §119 to Mexican Patent Application No. MX/a/2014/000944 with a filing date of Jan. 24, 2014, the disclosure of which is incorporated herein by reference in its entirety.

FIELD OF THE INVENTION

This invention relates to a high powered generator used to produce an electromagnetic field along hydrocarbon pipelines from a stabilized AC with a rectangular waveform whose measurements and interpretation is used for evaluating the state of the coating of the pipelines; which consists of five main modules: self-programmable regulated voltage power source module; power source reference decoupling module; H Bridge inverter module; feedback module, and control and processing module.

BACKGROUND OF THE INVENTION

In oil industry, metal pipelines are the main means of transportation and distribution of hydrocarbons. This is because they represent the most economical and safe solution for transferring over long distances and continuously outperforming transport efficiency by car-trunks (pipes), tank-trucks, trains and tankers. The need to achieve a timely supply of hydrocarbons has contributed, over time, to the installation throughout oil producer and consumer countries, of large networks of buried pipelines that during their exploitation process modify their technical and operational characteristics by several factors such as: deterioration caused by the environment surrounding them; pressure and temperature of the transported products; metal aging and its insulation, micro-tectonics movements, as well as the state of the cathodic protection system.

However, there are human factors that have impact in pipeline degradation such as: the improper handling during installation; inefficient state pipeline inspections and lack or poor maintenance works [Parker and Peattie, 1999]. All the aforementioned factors have as consequence the destruction of the insulation coating, development of corrosion and abrasion processes, reduction of wall-thickness of the pipeline and fractures. The effects of the deterioration of the pipes are reflected in economic loss and environmental damage.

Moreover, to ensure the integrity and operation of pipelines, methods of internal and external inspection are used. Internal methods are mainly used to evaluate fracture and corrosion on the walls of the pipelines. While to estimate damages in the coating and the cathodic protection system condition, nondestructive external electrical and electromagnetic methods are applied. The coating inspection of pipelines allows to detect areas or points of metal exposed to direct contact with the surrounding subsoil, being these areas or points of contact areas where corrosion is generated; besides, the inspections permit preventing metal corrosion avoiding breaks in pipelines and ecological disasters by hydrocarbons spills, thus reducing economic losses for damages, as well as higher costs in corrective maintenance.

Due to the pipeline being buried a few feet from the ground surface, the inspection of its coating can be done indirectly using electrical and electromagnetic methods.

Electrical methods such as CIPS (Close Interval Pipe-to-Soil Potential) [Pawson, 1998] and DCVG (Direct Current Voltage Gradient) [Masilela and Pereira, 1998] use electric field measurements of direct current to evaluate the effectiveness of the cathodic protection system and to locate defects in the coating. The pipeline-soil measurements are performed by synchronizing the on and off of the cathodic protection system and therefore, special equipment is required [Kho et al, 2007].

The disadvantage of these methods is their reliance on the resistivity of the medium as well as the pipeline depth, besides requiring prior knowledge of its position. However, these methods only provide qualitative information on damages of the coating and cannot be applied for the inspection of pipeline groups near or interconnected in shared rights of way.

To determine the path of the pipeline and the electrical quality of the coating, the PCM technique (Pipeline Current Mapper), which is based on measuring the magnetic field at the ground surface on the pipeline, is applied. The limitations of this methodology is that measurements can be performed at a maximum depth of 3 meters and cannot be applied in areas where there is pipeline congestion or crossing (separation between pipelines less than 4 times its depth) as overlapping of electrical fields occurs. Therefore, the determination of coating damage is qualitative.

The Superficial Electromagnetic Inspection Technology (TIEMS, in Spanish) allows one to assess the condition of the lining or coating of the pipelines from the emission of electromagnetic fields flowing radially on the environment that surrounds the pipeline and that are measured on the surface using sensors and synchronized receivers to the same frequency [Mousatov et al, 2004]. In the TIEMS it is approximated to the pipeline as electrical conductors of great length, presenting characteristics of capacitive and inductive reactors similarly to a transmission line when applying a periodic electrical signal. The processing of the measurements made on the surface allows to quantitatively obtain the value of the electrical resistance of the coating of the pipeline, identifying and delimiting the damaged areas. Likewise, to produce the electromagnetic field around the pipeline, it is used an external generator connected directly to the metal pipeline, proper management of their operational parameters are used: control type, magnitude, frequency and waveform of the transmitted signals, allow to extend the TIEMS scope as to be able to assess pipeline depths greater than 17 meters, interconnected pipelines and close share rights of via and to increase the resolution and inspection distances.

There are various types of commercial generators whose characteristics can be used to induce electromagnetic field around the pipeline, so it is important to note that the U.S. Pat. No. 6,051,977 patent, [Masuda et al, 2000] proposes a waveform generator capable of producing a variable signal which is connected directly to an amplifier block.

Moreover, in the generator proposed by Masuda, there is no way to perform a current control because there is not a block to monitor the system operating parameters. In the patent of [Masuda et al, 2000] a qualitative method is also proposed to evaluate through a moving vehicle, the coating condition of the pipeline, the proposed method is based exclusively on the detection of the magnetic field gradient along the pipeline axis and perpendicularly to it. There is no way to compensate variations in the depth of the pipeline, nor the effect of the surrounding environment, besides being applied only to detect damage in a single product.

However, in the design proposed by Pearson, in order to stabilize and keep constant the value of the output current [Pearson, 2004] it is considered a signal generator which controls the output power from a delta-sigma modulator, in this case there is feedback from the generator output to the modulator to achieve current stabilization. This design is characterized because after the power stage block exists a filtering block of the output signal of high power. The commercial equipment that protects the patent provides a combination of two or three simultaneous frequencies in sum sine (frequency combinations 4 Hz, 8 Hz, 98 Hz and 512 Hz), where the frequency used for the evaluation of the pipe is of 4 Hz, with preset intensities up to a maximum of 3 A and 50 Volts, so that it is possible to obtain a maximum output power of 150 watts. This maximum value limits the inspection of pipelines over 5 feet deep, and limits its scope along the pipeline.

Another option of generator is constituted by the ERA-MAX equipment, which provides one of six June preset frequencies to a maximum current of 200 mA with power output of 40 VA, the waveform of the output signal is rectangular and due to the low handling power, the scopes both in depth and length of the tube are smaller.

SUMMARY OF THE INVENTION

In this invention a high powered current generator for electromagnetic inspection of hydrocarbon pipelines is described. This generator is part of the specialized (TIEMS) instrumentation. The power generator supplies a square wave electrical signal, allowing the selection of frequencies within the range of 0.1 Hz to 1 KHz with a maximum deviation of 0.072%, to a programmable regulated current in the range of 0.1 amperes to 4.5 amperes with a stability of +−1 mA, the value selection is performed by the operator user and depends on the type of application to be performed.

One of the advantages of the generator object of this invention is that it provides an output power of 450 Watts, and has a temperature compensation system using two identical current sensors, one sensor that records the electrical regulated current output of the generator and another sensor obtains samples of operation drift of integrated circuit (IC) itself, and is used for compensation due to temperature variations of environment and operation; efficiently reaching an efficient operation up to 70° C. It also employs high power, high frequency switched-mode circuits as programmable voltage regulator, push-pull DC-AC inverter for electrical ground reference decoupling, and H-bridge DC-AC inverter to effect an efficient transfer of input-output power.

Another advantage is that it makes the electrical ground reference decoupling of power line in order to provide operational security. It also checks the voltage-current output relationship as self-protection system, not allowing exceeding the maximum operating power.

On the other hand the operating characteristics of the generator such as the use of the equipment in long predefined periods of time in hard environment conditions of humidity and temperature, and the portable design using autonomous energy systems, distinguish the generator in its application and use.

Nowadays, apart from high powered current generator for electromagnetic inspection of hydrocarbon pipelines, there is no other equipment operating efficiently under the conditions of soil moisture, temperature and characteristics of the pipelines in Mexico and that meet the electrical power and signal aspects required by the (TIEMS). Besides, the unique characteristics of the generator can be extended and applied to other geophysical studies and methods so there is the possibility of there is the possibility of performing various registers with a single generator, improving the performance and quality of the records.

BRIEF DESCRIPTION OF THE DRAWINGS

The present invention is described based on the figures whose brief description is as follows:

FIG. 6 shows the flowchart of the sequence of operation of the generator; and.

DETAILED DESCRIPTION OF THE INVENTION

This invention relates to a high powered current generator for electromagnetic inspection of the coating of hydrocarbon pipelines from an AC electric current stabilized and regulated with a rectangular waveform. The electrical regulated current is supplied to the pipeline to produce electromagnetic fields around and along such pipelines and whose measurements and interpretation is used for evaluating the state of the lining or coating of such pipelines. The high powered current generator consists of five main modules: programmable regulated voltage power source module; electrical ground reference decoupling module; H Bridge inverter module; feedback module, and control and processing module.

The generator object of the invention according to an exemplary implementation was specifically designed as part of the instrumentation of (TIEMS); which supplies an electric current in the pipeline to produce electromagnetic radiation along the hydrocarbon pipeline, this energy is detected over the surface of the soil by antennas to obtain the location of the pipeline and the electric current flowing therein. Said generator produces an alternating regulated current at a frequency that can be set within the range of 0.1 Hz to 1 KHz, however, to simplify the job of the operating personnel default values of, for example, 0.1, 0.2, 0.05, 1, 2, 4, 8, 98, 512 and 625 Hertz were established. The current value can also be programmed within the range of 0.1 A to 4.5 A, and to facilitate the work of the operators a set of fixed current values of 0.100, 0.250, 0.500, 1.0, 1.5, 2.0, 2.5, 3, 3.5, 4.0 and 4.5 Amperes was established.

Figure 1:
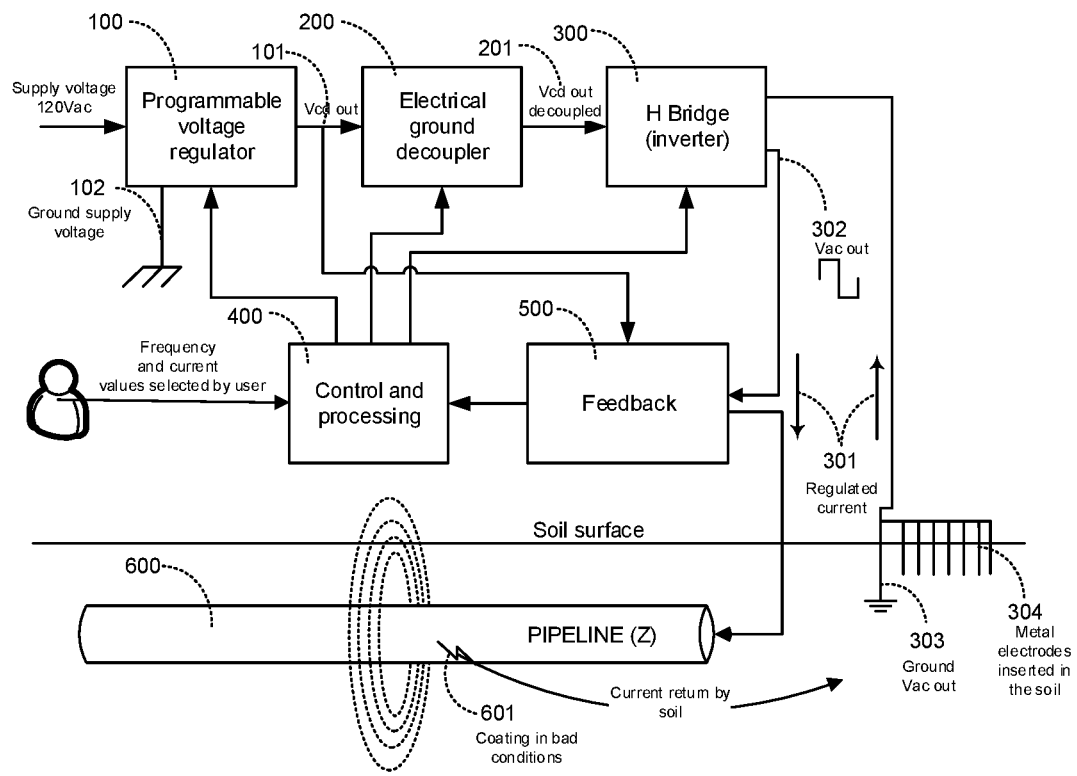
FIG. 1 shows the diagram in blocks of the constituent modules of the generator.
Figure 1A:
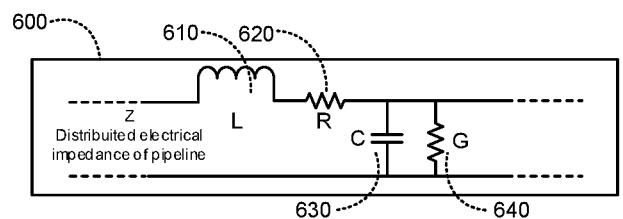
FIG. 1a shows the equivalent distributed impedance of a pipeline

FIG. 1 describes the diagram in blocks of the constituent modules of the generator; which contains a self-programmable voltage regulator [100], which feeds with a line voltage of 120 VAC at 60 Hz and provides a regulated DC voltage, Vcd out [101]; therefore, the value of the regulated DC voltage can be set from 10 to 130 VDC, depending on the selected electrical regulated current [301] and of the electrical impedance of the pipeline [600], based on the mathematical expression V=I×Z. FIG. 1.a show the pipeline's electrical impedance as a distributed electric circuit along the pipeline [600], formed by a distributed inductance L [610], a distributed resistance R [620], a distributed capacitance [630] and a distributed conductance G [640]. The electrical regulated current [301] from power generator flows through feedback module [500], pipeline [600], escapes from pipeline at damaged coating [601], continues by soil where pipeline is buried, and finally is collected by metal electrodes [304] inserted into the soil. The regulated voltage, Vcd out [101], is decoupled from the electrical ground reference [102] of the voltage of the power line through a decoupler [200].

Moreover, the H-Bridge inverter [300] converts the regulated DC voltage [201] into square wave AC voltage [302] of frequency selected by user, and the feedback module [500] conditions the samples of the values of the self-programmable voltage regulator output [101] and of the current output [301] of the H-Bridge inverter [300] which is supplied to the pipeline [600]; afterwards, the voltage and current samples are processed by the control circuit [400], which determines the value of the output voltage [101] of the programmable voltage regulator [100] to produce the regulation of output current [301], also the control circuit [400] determines the square wave frequency [302] and provides the user interface for the computer-user interaction.

Figure 2:
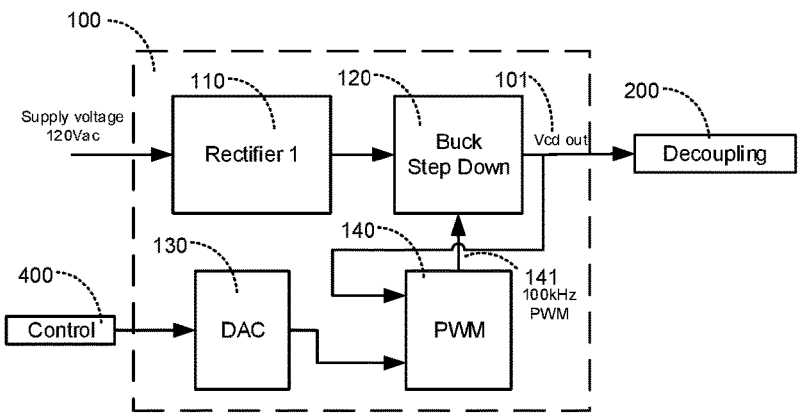
FIG. 2 shows the diagram in blocks of the programmable voltage regulator module.

However, the self-programmable voltage regulator power source module [100] of FIG. 2 contains a rectifier circuit 1 [110], a power supply switching step down Buck [120] controlled by the PWM circuit [140] and the digital analog converter DAC [130]. Rectifier 1 circuit [110] converts AC power of 120 VAC, 60 Hz, to a DC voltage of 168 VDC. Moreover, the step-down Buck circuit [120] provides a regulated DC voltage, Vcd out [101], in the range from 10 to 130 VDC. The value of the regulated voltage is set by the control block [400] placing a digital data into the digital to analog converter DAC [130]. The PWM circuit [140] compares the voltage that gives the DAC [130] with the feedback signal of the Buck output [120] to produce a frequency square signal of 100 KHz [141] modulated in the pulse width (PWM).

Figure 3:
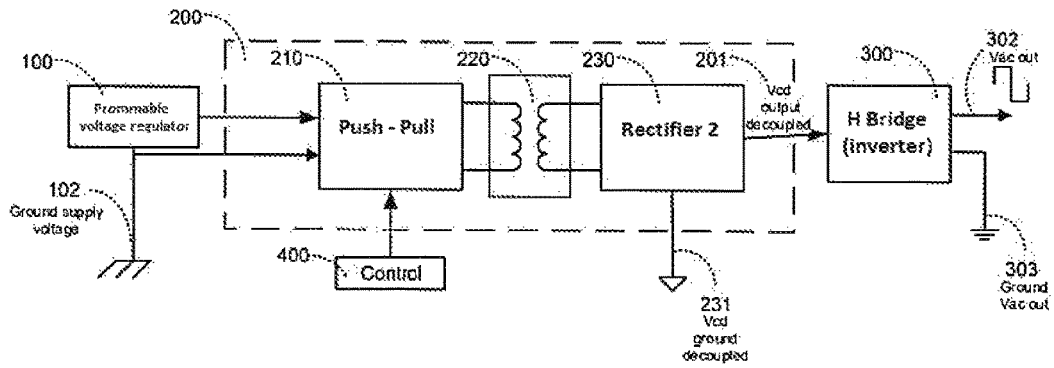
FIG. 3 shows the diagram in blocks of the electrical ground decoupler module.

The stage of the electrical ground decoupler module [200] of FIG. 3, isolates the supply voltage electrical ground reference from 120 VAC [102] relative to the output voltage ground of the generator output [303]. This decoupling stage [200] is comprised of a high frequency Push-Pull DC-AC inverter circuit [210], a high-frequency-high current transformer [220] and a high frequency Rectifier 2 circuit [230]. The Push-Pull DC-AC inverter circuit [210] feeds from the programmable voltage regulator module [100] to produce an AC voltage in the primary of the transformer [220] with frequency of 50 KHz. Also, the control circuit [400] sets the frequency of 50 KHz, where the AC voltage at the output of secondary winding of the transformer [220] becomes in DC voltage at the output of the Rectifier 2 circuit [230]. Finally, said decoupling stage [200] provides a continue DC voltage [201] ranging from 8V to 100V.

The H Bridge inverter module [300] (FIG. 1), alternates the current at the generator output system [302] at a frequency of 0.1 Hz to 1 KHz; therefore, the operating frequency is set by the stage of the control circuit [400].

Moreover, the feedback module [500] (FIG. 1), conditions the Vcd output [101] and regulated current [301] as feedback signals and sends theses to the control and processing module [400] to establish the voltage output [101] of the programmable voltage regulator [100] and the electrical current output [302] of the H Bridge inverter [300].

Figure 4:
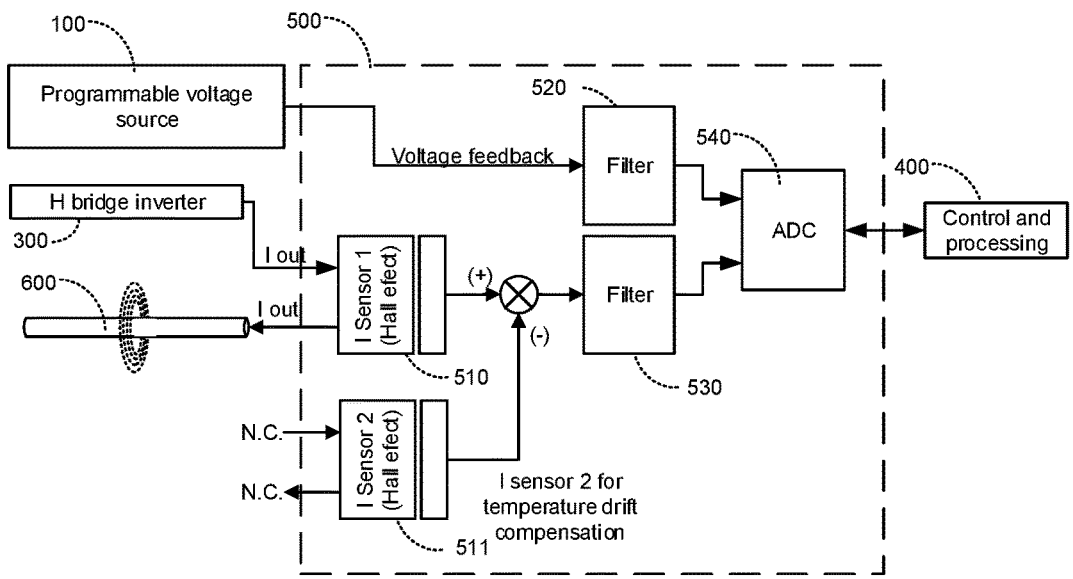
FIG. 4 shows the diagram in blocks of the inverter module.

However, in FIG. 4 the feedback module [500] is described, and comprises: a sensor 1 of high current Hall Effect [510]; a sensor 2 of high current Hall Effect [511]; two low pass filters [520] and [530] and an ADC analogical to digital converter [540]. The Hall Effect [510] current sensor 1 gets the value of the output current of the generator; thus, a sample value of the programmable voltage regulator [100] is obtained by a voltage divider. Both analogical signals are subjected to low-pass filters [520] [530] and to analog-digital conversion [540] for then being supplied to the stage control circuit [400]. The sensor 2 [511] is not connected in its input, but suffer the same drifts by temperature as sensor 1 [510] so the signal of sensor 2 [511] is subtracted from signal of sensor 1 [510] to compensate signal variations due to environment and operation temperature.

Figure 5:
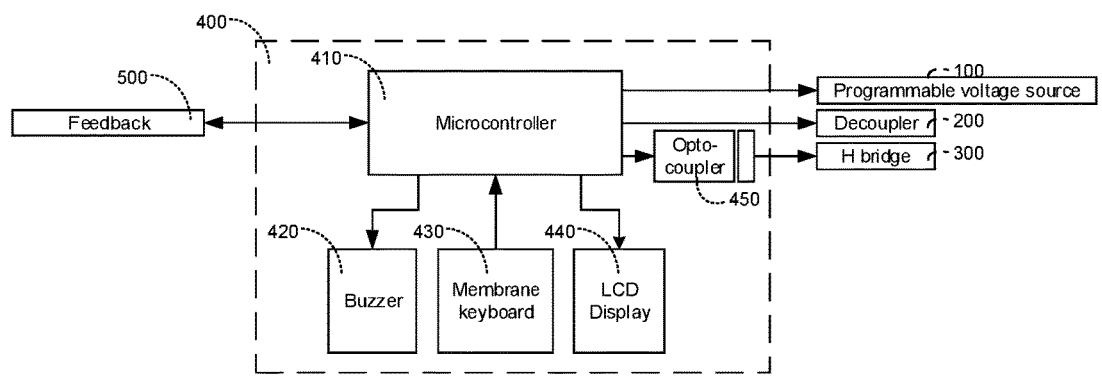
FIG. 5 shows the diagram in blocks of the control module.

The control circuit stage [400] in FIG. 5, comprises a microcontroller [410], a membrane keyboard [430], a liquid crystal display LCD [440] and a piezoelectric buzzer [420]. Said controlling stage [400], bases its operation on a firmware software contained on the microcontroller [410], performing the following functions: Operations menu display and current voltage and frequency parameters, through the LCD [440]; obtaining the operating instructions or commands via the membrane keyboard [430]; regulation of the output current through the programmable voltage regulator [100] and generation of the output frequency of the H-Bridge inverter [300], so the generating signal of the output frequency goes through a optocoupler [450] Also the 50 KHz square wave signal needed for ground decoupling [200] is generated.

TABLE 1

High Powered Current Generating Equipment Specifications
The power generator is a set of electronic cards and electric elements confined in a high resistance container to rough use.

| | |
|---|---|
| Power | 117 VAC; 5 A; 60 Hz |
| Output Power | 450 VA |
| Maximum output voltage | 100 VAC |
| Regulated output current (selectable) | {0.100, 0.250, 0.500, 1.0, 1.5, 2.0, 2.5, 3, 3.5, 4.0, 4.5} Amperes |
| Current resolution | 0.003 Amperes |
| Output frequency (selectable) | {0.1, 0.2, 0.5, 1, 2, 4, 8, 98, 512 and 625 Hertz} |
| Frequency resolution | ±0.001% Hz full scale |
| Output signal | Square waveform |
| Operating temperature | 50° C. maximum |
| Operating Humidity | 70% maximum |
| Dimensions | 47 × 35.7 × 17.6 cm |
| Weight | 10 Kg |

Description of the Firmware Software.

The software on the microcontroller of power generator was developed in ANSI C programming language. The functions performed by the firmware are:

Configuring and controlling the operation of the system.
Displaying Information and operation sequence.
Interface with the operator user via the membrane keyboard [430] and the liquid crystal display (LCD) [440].
Generation and Frequency Control: Frequency of electromagnetic energy (from 0.1 Hz to 1 kHz) supplied to the H Bridge [300]; frequency of 100 KHz [141] required in the PMW [140] for the current regulation and frequency of 50 KHz required in the electrical ground reference decoupling stage [200].
Regulation of the output current. Algorithm reading "True RMS" of the feedback current and adjustment of the error signal with the desired operating current.

Limiting control of the maximum output power up to 450 Watts. Overload protection algorithm.

Figure 6:
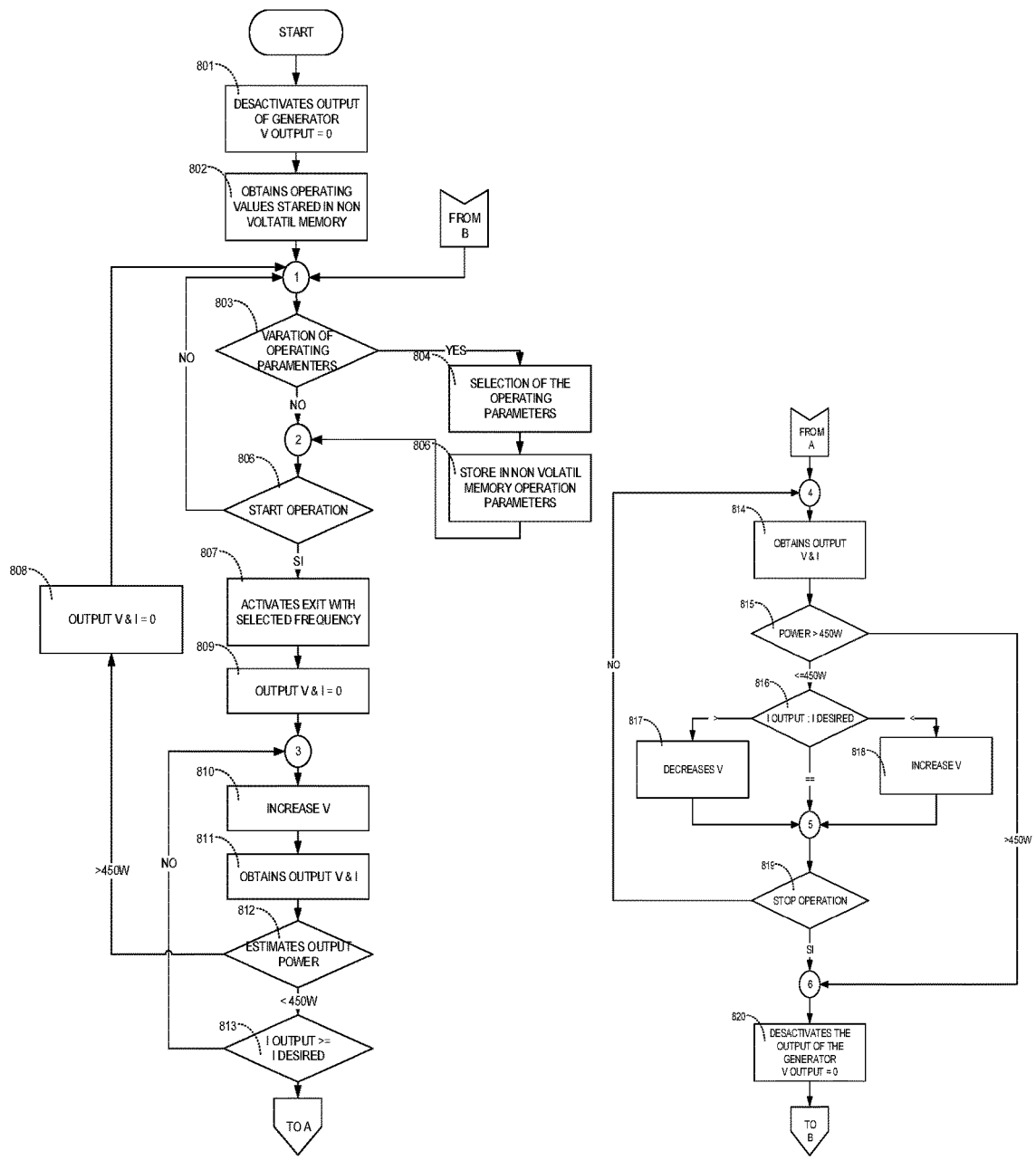
Figure 7:
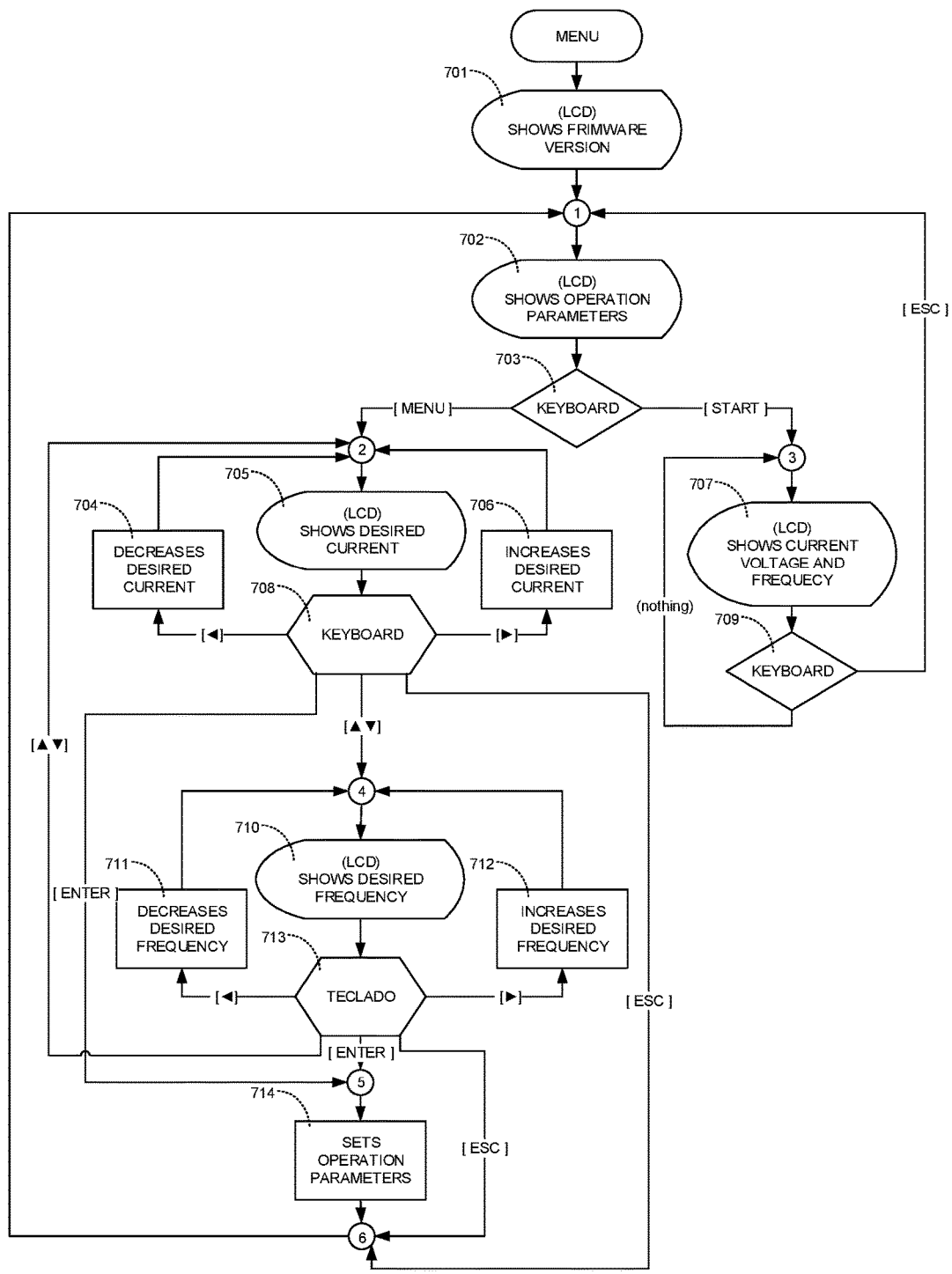
FIG. 7 shows the flowchart of the current selection and operating frequency.

On the other hand, on the flowchart of FIGS. 6 and 7, the configuration sequence and the operation of the generator are respectively described respectively:

When powering up the equipment, the system boots getting the pre-set values of operation and the output current zero [801] is set.

It initializes and configures the display.

The display shows the menu options "start operation-configure system" [702] [803] [806] and waits for the user operator action via the keyboard [703].

If the operator chooses to start the operation [806], it increases slowly and gradually the output current [810] from zero [809] to the selected operating current [813]. Output power [812] is evaluated, restarting the system if the 450 watts are exceeded.

Upon reaching the desired current [813], it is entered into regulation operation the current control operation evaluating current feedback with the desired current [816] and the output [815]. The value of the output voltage is increased [818] if the output current is less than the desired current. The value of the output voltage is decreased [818] if the output current is greater than the desired current.

If the output power exceeds from 450 watt [815], the current output is set to zero [820] and returns to the menu of options "start operation—set system" [702] [803] [806].

If the operator chooses to configure operating parameters [803] [703], it is allowed to configure the frequency and output current [804] [805] [710] [705].

Using the up and down key arrows in the keyboard [708] [713], the operator can select between configuring current or configuring frequency [705] [710].

Using the left and right key arrows in the keyboard [704] [706], the operator can select the desired current value, which can be 0.100, 0.250, 0.500, 1.0, 1.5, 2.0, 2.5, 3, 3.5, 4.0 or 4.5 amperes.

Using the left and right key arrows in the keyboard [711] [712], the operator can select the value of operating frequency and can be 0.1, 0.2, 0.5, 1, 2, 4, 8, 98, 512 or 625 Hz.

With the ENTER key [713] the operator sets the selected values as operating value [714] and returns to the menu "start operation—set system" [702] [803] [806] [806].

With the ESC key [708] [713] the operator can abort the selection of parameters, leaving as operating parameters the previous values and returns to the "start operation—set system" [702] [803] [806].

Field Trials

The generator object of this invention was tested in field operations for the inspection of the state of coating of the pipeline. Measurements equipment for the monitoring of operating parameters; electrical current stability, high frequency stability, maximum percentage of output current variation were connected. The results obtained were the following

TABLE 2

| Experimental Operation Technique Characteristics | |
| --- | --- |
| PARAMETER | Final outcome |
| Current | 0 to 4.5 amperes |
| Total power | 450 watts |

TABLE 2-continued

| Experimental Operation Technique Characteristics | |
| --- | --- |
| PARAMETER | Final outcome |
| Output voltage | 100 v |
| Stability in Frequency | 99.9% |
| Resolution in Frequency | 0.001% full scale |
| Stability in current | +/−3 mA |
| Weight of the equipment | 9 Kg |
| Maximum percentage of output variation | 0.2% |

CITED FOREIGN REFERENCES

[Kho et al, 2007] Y. T. Kho, J. Y. Jcon, K. W. Park, Y. B. Cho, "DCVG_CIPS Measuring apparatus for detecting the results of a pipe line". U.S. Pat. No. 7,292,052 B2, Korea Gas Corporation. 2007.

[Masuda et al, 2000]. Method and apparatus for locating coating faults on buried pipelines. Masuda Toshikazu, Osada Toshio, Gotoh Shingi. U.S. Pat. No. 6,051,977, Apr. 18, 2000.

[Pearson, 2004]. Richard David Pearson. "Signal Generator". U.S. Pat. No. 6,836,231 B2. Radiodetection Limited. 2004.

[Pawson, 1998] R L Pawson: "Close Interval Potential Surveys—Planning, Execution, Results", Corrosion, paper 575 pp. 10 Feb. 1998.

[Masilela and Pereira, 1998] Z. Masilela and J. Pereira: "Using the DCVG technology as a quality control tool during construction of new pipelines," Engineering Failure Analysis, Vol 5, No. 2, pp. 99-104, 1998.

OTHER REFERENCES

[Mousatov et al, 2004]. Mousatov A., E. Nakamura, V. Shevnin. "Electromagnetic surface method for the pipeline periodical inspection based on the heterogeneous transmission line model". Proceeding on V International Pipeline Conference, Calgary Alberta, Canada, October 2004.

[Parker and Peattie, 1999]. M. Parker, E. Peattie. "Pipe Line Corrosion and Cathodic Protection". Third edition. Gulf Professional Publishing. Elsevier Science USA.

[Alpin, 1939]. L. M. Alpin, "Technology of electrical logging in borehole with casing". Patent N56026, 30 Nov. 1939, priority from 20 Feb. 1937. (In Russian). 1939.

What is claimed is:

1. A high powered current generator for electromagnetic inspection of hydrocarbon pipelines, wherein a stabilized alternating current of rectangular waveform is used for evaluating the condition of a coating of the pipeline, the generator comprising: 1) a programmable voltage regulator module, to set a value of a regulated voltage from about 10 to 130 VDC, based on a regulated electrical current of operation and an electrical impedance of a pipeline according to the equation $V=I \times Z$, where V is the voltage, I is the current and Z is the impedance; 2) an electrical ground reference decoupling module, for isolating a ground supply voltage from VAC input with respect to an output voltage of the generator; 3) an H Bridge inverter module, which allows alternating current of the generator output at a frequency of about 0.1 Hz to 1 KHz; 4) a feedback module that acquires and performs analog to digital sample conversion of voltage and electrical current from a programmable voltage regulator module output and from the H-bridge inverter module output supplying digital feedback signals to the control and processing for setting the output of the programmable voltage regulator module and regulating current output of the generator; 5) and a control and processing module that contains a microcontroller with firmware for regulating output electrical current, self-protection to over-power generator output, and generation of frequencies of operation.

2. The generator of claim 1, having a temperature compensation system to compensate operation drifts of the generator caused by temperature variations, said compensation system comprising a first current sensor to record temperature variations and a second current sensor to record current variations.

3. The generator of claim 1, wherein a self-programmable voltage regulation is performed for current regulation and effect of an efficient transfer of the input-output power by a programmable voltage regulator including step-down buck circuit for programmable voltage, high frequency push pull circuit for decoupling electrical ground, and high power H-bridge circuit for alternating electrical regulated current output at a predetermine operation frequency.

4. The generator of claim 1, comprising a self-protection system including firmware in the microcontroller to prevent damage of electrical parts of the generator by preventing exceeding the maximum operating power over 450 watts.

5. The generator of claim 1, wherein a frequency in a range of 0.1 Hz to 1 kHz and programming of output stabilized in a range from 0.1 amps to 4.5 amperes is based on a square wave electrical signal supplied to the pipeline, where frequency and current are selected by a user via a keyboard and LCD of the control and processing module.

* * * * *